United States Patent
Saleh Almulhim

(10) Patent No.: US 11,737,763 B1
(45) Date of Patent: Aug. 29, 2023

(54) LAPAROSCOPE FOR INSTALLING SURGICAL CLIPS

(71) Applicant: KING FAISAL UNIVERSITY, Al-Ahsa (SA)

(72) Inventor: Abdulrahman Saleh Almulhim, Al-Ahsa (SA)

(73) Assignee: KING FAISAL UNIVERSITY, Al-Ahsa (SA)

( * ) Notice: Subject to any disclaimer, the term of this patent is extended or adjusted under 35 U.S.C. 154(b) by 0 days.

(21) Appl. No.: 18/127,243

(22) Filed: Mar. 28, 2023

(51) Int. Cl.
*A61B 17/128* (2006.01)
*A61B 17/00* (2006.01)

(52) U.S. Cl.
CPC ............. *A61B 17/1285* (2013.01); *A61B 2017/00818* (2013.01)

(58) Field of Classification Search
CPC .............. A61B 17/128; A61B 17/1285; A61B 2017/00818
See application file for complete search history.

(56) References Cited

U.S. PATENT DOCUMENTS

| | | | | |
|---|---|---|---|---|
| 4,274,415 A * | 6/1981 | Kanamoto | ......... | A61B 17/1227 606/221 |
| 4,556,060 A * | 12/1985 | Perlin | ................ | A61B 17/1227 24/552 |
| 4,976,722 A * | 12/1990 | Failla | ................... | A61B 17/122 606/151 |
| 4,979,950 A * | 12/1990 | Transue | ............... | A61B 17/122 606/158 |
| 5,156,608 A * | 10/1992 | Troidl | ................ | A61B 17/1285 227/901 |
| 5,496,310 A * | 3/1996 | Exconde | ................ | A61B 17/29 606/205 |
| 5,556,411 A | 9/1996 | Taoda et al. | | |
| 6,350,269 B1 * | 2/2002 | Shipp | ................. | A61B 17/1285 606/151 |
| 6,488,691 B1 | 12/2002 | Carroll et al. | | |
| 7,713,276 B2 * | 5/2010 | Dennis | ............... | A61B 17/1227 606/151 |
| 10,064,623 B2 * | 9/2018 | Soutorine | ............ | A61B 17/122 |
| 11,253,282 B2 * | 2/2022 | Belman | ................ | A61B 17/285 |
| 11,642,206 B1 * | 5/2023 | Almulhim | ............. | A61F 2/0063 606/151 |
| 2005/0021062 A1 * | 1/2005 | Dennis | ............... | A61B 17/1227 606/157 |
| 2008/0188872 A1 * | 8/2008 | Duff | ................... | A61B 17/1285 606/142 |
| 2014/0058411 A1 * | 2/2014 | Soutorine | ............ | A61B 17/128 606/151 |
| 2019/0282255 A1 * | 9/2019 | Belman | ............ | A61B 17/12009 |

* cited by examiner

*Primary Examiner* — Ryan J. Severson
(74) *Attorney, Agent, or Firm* — Nath, Goldberg & Meyer; Richard C. Litman

(57) ABSTRACT

A system, device, and method for clamping off a cystic artery or cystic duct during a cholecystectomy includes using a trio of surgical clips which are released from a clip applicator in a simultaneous fashion so that the cystic artery and cystic duct are clamped off using only a single trigger firing operation from the clip applicator.

12 Claims, 1 Drawing Sheet

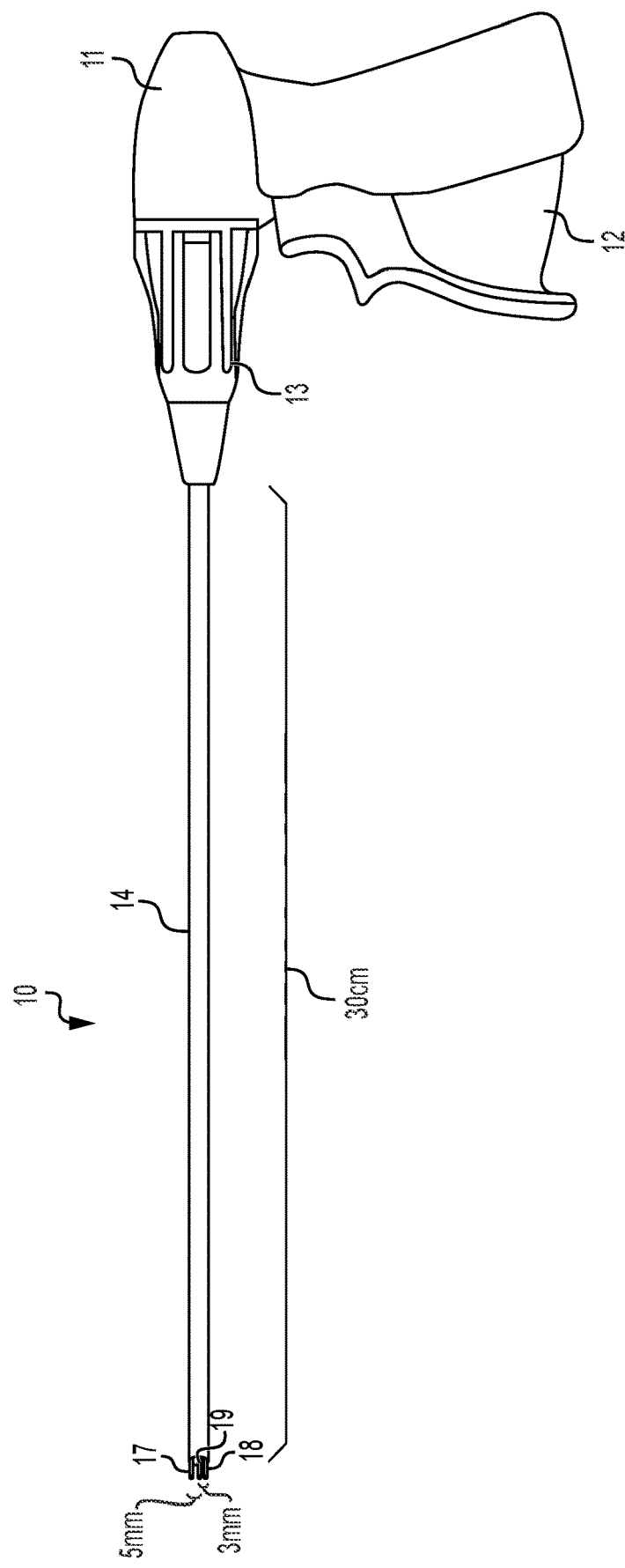

LAPAROSCOPE FOR INSTALLING SURGICAL CLIPS

BACKGROUND

1. Field

The present disclosure relates to gastrointestinal procedures and devices, and particularly to a laparoscopic method and device for clipping the cystic duct and cystic artery during cholecystectomy surgical procedures.

2. Description of the Related Art

One of the most common surgical procedures performed around the world today is a laparoscopic cholecystectomy. Laparoscopic cholecystectomy is a minimally invasive surgical procedure used for the removal of a diseased gallbladder. Since the early 1990s, this technique has largely replaced the open technique for cholecystectomies. Laparoscopic cholecystectomy is currently indicated for the treatment of acute or chronic cholecystitis, symptomatic cholelithiasis, biliary dyskinesia, acalculous cholecystitis, gallstone pancreatitis, and gallbladder masses or polyps. The surgery involves removing the gallbladder along with the cystic artery and cystic duct connections of the gallbladder. To seal off the cystic artery and cystic duct, spring-loaded surgical clips are used to clamp off the section of the cystic duct and cystic artery that are severed to remove the undesired gallbladder during the surgical procedure.

The gallbladder lives on the inferior aspect of the liver bed, can be up to 10 cm in length, and physiologically can hold up to 50 cc of fluid (bile). A line from the gallbladder to the inferior vena cava separates the liver into right and left lobes. There are four anatomical sections to the gallbladder: fundus, body, infundibulum, and neck. There is great variation in the biliary ductal anatomy. The cystic duct most commonly arises from the common bile duct and inserts at the neck of the gallbladder. The branch point of the cystic duct from the common bile duct marks the beginning of the common hepatic duct superiorly. The blood supply to the gallbladder is from the cystic artery which originates approximately 90% of the time from the right hepatic artery. Again, there is great variation in the course and origin of the cystic artery. The hepatocytic triangle (triangle of Calot) is a surgical anatomical landmark created by the cystic duct laterally, the common hepatic duct medially, and the liver edge superiorly. This triangle is of surgical importance because this is the location for the most common path of the cystic artery to the gallbladder. The sentinel lymph node of the gallbladder resides within the hepatocytic triangle, also known as Lund's node.

After induction of anesthesia and intubation, the laparoscopic cholecystectomy may begin. First, insufflation of the abdomen is achieved to 15 mmHg using carbon dioxide. Next, four small incisions are made in the abdomen for trocar placement. Utilizing a camera (laparoscope) and long instruments the gallbladder is retracted over the liver. This allows for exposure of the proposed region of the hepatocytic triangle. Careful dissection is carried out to achieve the critical view of safety. This view is defined as (1) clearance of fibrous and fatty tissue from the hepatocytic triangle, (2) the presence of only two tubular structures entering the base of the gallbladder, and (3) the separation of the lower third of the gallbladder from the liver to visualize the cystic plate. Once this view is adequately achieved, the operating surgeon can proceed with confidence that he/she has isolated the cystic duct and cystic artery. Both structures are carefully clipped and transected. An electrocautery or harmonic scalpel is then used to separate the gallbladder from the liver bed completely. Hemostasis should be achieved after the abdomen is allowed to deflate to 8 mm Hg for 2 minutes. This technique is employed to avoid missing potential venous bleeding that can be tamponaded by elevated intra-abdominal pressure (15 mm Hg), and thus the gallbladder can be removed.

Those skilled in the art will appreciate that the use of surgical clips for homeostasis or ligation is well-known. U.S. Pat. Nos. 4,976,722 and 4,979,950 describe prior art clips that are formed of titanium wire. Application of these prior art clips is normally accomplished by means of a crushing action produced by a clip applier where such a crushing action irrevocably deforms one clip into the desired shape for deployment, making it impossible to remove or reposition them. Another problem with crush clips is that vessels and tissue often shrink after occlusion owing to the onset of necrosis.

Some clips, such as those described in U.S. Pat. No. 4,556,060, are designed for placement on the tissue in the surgical field by hand. Other clips, such as those described in U.S. Pat. No. 4,274,415, are applied using applicators for use in open surgeries but not in the confined surgical environment of laparoscopic surgeries. One applicator that is suitable for use in laparoscopic surgeries is the applicator disclosed in U.S. Pat. No. 6,350,269. However, the clip and applicator combination of the '269 patent has several problems. The first of which is that the clip is designed to have a narrow proximal end and the feed track in the clip holder is relatively wide. This arrangement causes the clip to stack to kink, further causing additional excessive friction during the clip feeding process, which can result in the clip pusher slipping over clips and/or clips jamming. Also, since the jaws of the applicator are necessarily wide, this does not allow adjacent clips to be placed in close proximity to each other as is often required in complex and delicate procedures such as cholecystectomies.

In cholecystectomies, a series of clips must be applied in a quick and synchronized fashion to the severed cystic artery and cystic duct where the placement of the three dips is in close proximity to one another. Accordingly, what is needed is a laparoscopic applicator that can insert a trio of surgical clips simultaneously to the surgical field of a cholecystectomy such that the clips can simultaneously clamp off the severed portions of the cystic artery and the cystic duct in a single operation, thereby shortening the procedure time and minimizing a patient's time on the operating table. Thus, a device to assist with laparoscopic surgery solving the aforementioned problems is desired.

SUMMARY

The present laparoscopic method, system, and device provide for the use of a clip applicator attachment on the distal end of the device, where the clip applicator attachment has three clips ready for deployment into the surgical field such that the clips are applied at a fixed safe distance during a laparoscopic procedure, such as a cholecystectomy in a patient. The application of the clips is effected through a single trigger squeeze of the clip applicator. The clips are held in place by a clip guide attachment which is affixed to the distal end of the clip applicator where each clip in the clip guide is affixed in position at a fixed distance with prescribed distance intervals between the three clips. When deployed simultaneously, the trio of clips clamp down on the severed portions of the cystic artery and cystic duct so the gallbladder can be quickly excised from the surgical field.

These and other features of the present subject matter will become readily apparent upon further review of the following specification.

BRIEF DESCRIPTION OF THE DRAWINGS

FIG. 1 is a perspective view of a laparoscopic device with a clip attachment on the distal end of the clip applicator.

Similar reference characters denote corresponding features consistently throughout the attached drawings.

DETAILED DESCRIPTION OF EMBODIMENTS

The laparoscopic method and device for clamping a cystic artery and cystic duct during a cholecystectomy is provided herewith mainly as a complement to a standard laparoscope, endoscope, gastroscope, or colonoscope in that it is adaptable to the particular configuration of the scope and no scope needs to be specially modified to practice the method and the device that accompanies the method.

In the detailed view provided by FIG. 1, the clip applicator is shown and generally designated by the numeral 10. Applicator (10) includes a body or handle subassembly (11) and a rotator subassembly (13). The handle subassembly (11) comprises two handle halves. The rotator subassembly also comprises two halves and houses a surgical clip holder (not shown), and mates to an actuator tube (14), A plurality of clips is housed within the clip holder. The two rotator subassembly halves are held together by friction from alignment pins in a first of the rotator subassembly halves and a corresponding series of mating sockets in a second of the rotator subassembly halves (not shown) or by welding or otherwise bonding the halves together.

The proximal end of the rotator subassembly connects to the handle subassembly (11) which includes a grip portion and a trigger (12) where the hand of the user would wrap around the grip portion of the handle subassembly (11) and the trigger is squeezed towards the handle subassembly (11) by the same hand of the user when a trio of clips is to be released into place from the distal end of the actuator tube (14). After the trigger is squeezed, the trigger reverts to a ready to fire position which has the trigger (12) extended apart from the handle subassembly (11). A clip guide (not shown) has a collection of U-shaped clips (17), (18), (19) in fixed positions along a distal surface of the clip guide with a fixed distance between clips (17) and (19) being about 5 mm, a fixed distance between clips (18) and (19) being about 3 mm, and a fixed distance between clips (17) and (18) being about 8 mm.

When the trigger (12) is squeezed, the three U-shaped clips (17), (18), and (19) are simultaneously inserted into the surgical field at the fixed distances as prescribed above such that the clips can be used to clamp off the cystic artery and cystic duct. When the trigger is let go and extends back to the ready to fire position, three replacement clips from the clip holder are loaded into the clip guide by being fed through the actuator tube (14) from the rotator subassembly (13) to the distal end of the applicator (10) where the clip guide is affixed. The three replacement clips are moved into place at the same fixed distances. Within the actuator tube (14) is a push rod (not shown) that moves the replacement clips down the actuator tube to the clip guide.

Each individual surgical clip can be manufactured using wire of rectangular, circular, or other constant cross-sectional shapes. In an embodiment, the wire has a circular cross-sectional shape and is made from implantable metal or a metal alloy such as titanium. The clip is formed in an inverted U-shape with clip engagement fingers on either side so that a clip pusher only needs to clear the clip guide while resetting.

As previously noted, the applicator (10) is especially constructed for use in laparoscopic surgery wherein the applicator must be inserted through as small an opening as possible in the patient's body, although it can be readily used in open surgery procedures as well.

It will be understood that the clips may be loaded into the clip holder without any consideration to any up or down clip orientation since the clips are symmetric in that regard. The symmetry eliminates orientation mistakes during the manufacturing process.

It is to be understood that the endoscopic method and device for sealing a gastrointestinal defect is not limited to the specific embodiments described above but encompasses any and all embodiments within the scope of the generic language of the following claims enabled by the embodiments described herein, or otherwise shown in the drawings or described above in terms sufficient to enable one of ordinary skill in the art to make and use the claimed subject matter.

I claim:

1. A laparoscopic method for performing a cholecystectomy on a patient using a dip applicator, comprising:
    loading a plurality of surgical clips into a clip holder of said clip applicator;
    positioning a distal end of a clip applicator near a surgical field of a gallbladder to be removed from the patient;
    positioning a first, a second, and a third surgical dip near a severed portion of a cystic artery and a severed portion of a cystic duct of the patient;
    squeezing a trigger on the clip applicator wherein the first, second, and third surgical clips are released simultaneously from the clip applicator and simultaneously clamp onto the to severed portion of the cystic artery and the severed portion of the cystic duct;
    securing the severed portion of the cystic artery and the severed portion of the cystic duct; and
    removing the gallbladder from the surgical field.

2. The laparoscopic method for performing a cholecystectomy using a clip applicator as recited in claim 1, wherein said first, second, and third surgical clips are U-shaped.

3. The laparoscopic method for performing a cholecystectomy using a clip applicator as recited in claim 2, wherein said first, second, and third surgical clips are symmetrical.

4. The laparoscopic method for performing a cholecystectomy using a clip applicator as recited in claim 3, wherein said first, second, and third surgical clips are made from an implantable metal or metal alloy.

5. The laparoscopic method for performing a cholecystectomy using a clip applicator as recited in claim 4, wherein said implantable metal or metal alloy is titanium.

6. The laparoscopic method for performing a cholecystectomy using a clip applicator laparoscopic method for performing a cholecystectomy using a clip applicator as recited in claim 1, wherein said first, second, and third surgical clips are spaced at a fixed distance apart where said fixed distance between the first and second clips is about 5 mm, between the second and third clips is about 3 mm, and between the first and third clips is about 8 mm.

7. A device for use with a laparoscope for performing a cholecystectomy using a clip applicator, comprising:
- a rotator subassembly for loading a plurality of surgical clips into a clip holder of said clip applicator;
- a handle subassembly for positioning a distal end of a clip applicator near a surgical field of a gallbladder to be removed;
- an actuator tube for positioning a first, a second, and a third surgical clip near a severed portion of a cystic artery and a severed portion of a cystic duct; and
- a trigger on the clip applicator which, when squeezed, releases the first, second, and third surgical clips from the clip applicator to simultaneously clamp onto the severed portion of the cystic artery and the severed portion of the cystic duct.

8. The device for use with a laparoscope for performing a cholecystectomy using a dip applicator as recited in claim 7, wherein said first, second, and third surgical clips are U-shaped.

9. The device for use with a laparoscope for performing a cholecystectomy using a dip applicator as recited in claim 8, wherein said first, second, and third surgical clips are symmetrical.

10. The device for use with a laparoscope for performing a cholecystectomy using a clip applicator as recited in claim 9, wherein said first, second, and third surgical clips are made from an implantable metal or metal alloy.

11. The device for use with a laparoscope for performing a cholecystectomy using a clip applicator as recited in claim 10, wherein said implantable metal or metal alloy is titanium.

12. The device for use with a laparoscope for performing a cholecystectomy using a clip applicator as recited in claim 7, wherein said first, second, and third surgical clips are spaced at a fixed distance apart, where said fixed distance between the first and second clips is about 5 mm, between the second and third clips is about 3 mm, and between the first and third clips is about 8 mm.

* * * * *